US010655283B2

(12) United States Patent
Andersson

(10) Patent No.: US 10,655,283 B2
(45) Date of Patent: May 19, 2020

(54) METHOD OF DETERMINING THE QUALITY OF A NEWLY PRODUCED ASPHALT PAVEMENT

(71) Applicant: CA KONSULT, Bollebygd (SE)

(72) Inventor: Conny Andersson, Bollebygd (SE)

(73) Assignee: CA KONSULT, Bollebygd (SE)

( * ) Notice: Subject to any disclaimer, the term of this patent is extended or adjusted under 35 U.S.C. 154(b) by 274 days.

(21) Appl. No.: 15/576,738

(22) PCT Filed: Jun. 3, 2016

(86) PCT No.: PCT/EP2016/062647
§ 371 (c)(1),
(2) Date: Nov. 24, 2017

(87) PCT Pub. No.: WO2016/198333
PCT Pub. Date: Dec. 15, 2016

(65) Prior Publication Data
US 2019/0003134 A1    Jan. 3, 2019

(30) Foreign Application Priority Data

Jun. 10, 2015 (SE) .................................. 1550776-7

(51) Int. Cl.
*E01C 23/01* (2006.01)
*E01C 19/48* (2006.01)
(Continued)

(52) U.S. Cl.
CPC .............. *E01C 23/01* (2013.01); *E01C 19/48* (2013.01); *G01N 25/72* (2013.01); *G01N 33/42* (2013.01)

(58) Field of Classification Search
None
See application file for complete search history.

(56) References Cited

U.S. PATENT DOCUMENTS 6,122,601 A     9/2000 Swanson
6,749,364 B1 *  6/2004 Baker .................... E01C 19/288
                                                   404/118
(Continued)

FOREIGN PATENT DOCUMENTS

CN     102691251     9/2012
RU     105307       6/2011
(Continued)

OTHER PUBLICATIONS

Office Action issued in corresponding Russian Patent Application No. 2017144240/03 , dated Sep. 16, 2019, pp. 1-6, and English translation pp. 1-3.
(Continued)

*Primary Examiner* — Leslie J Evanisko
*Assistant Examiner* — Leo T Hinze
(74) *Attorney, Agent, or Firm* — Jeffrey S. Melcher; Melcher Patent Law PLLC

(57) ABSTRACT

This invention relates to a method to determine the quality of an asphalt pavement, the method comprising the steps of: a) providing and initializing at least one sensor (1) connected to a processor arrangement (2) comprising at least one processor (20A, 20B) connected to at least one memory (21A, 21B), for recording at least the temperature values (Tn), time (t) and/or position (X) momentarily for the entire width (W) of an asphalt pavement (4) in connection with its production along a pavement path (X) b) scanning and registering a number (P) individual temperature ranges (TIn) for a number (P) of the section ranges (ΔX') in a section (ΔX) c) compiling said temperature ranges (TIn) in said section (ΔX) distributed along said width (W) d) determining and storing in said memory (21) an average temperature range (TIm) presenting an average temperature range (TIm) for the said number (P) of compiled temperature ranges (Continued)

(TIn) distributed along said width (W) of said section (ΔX), e) repeating steps b) to d) until all of said pavement distance (X) is produced, wherein said stored average temperature ranges (TIm), in said memory (21), are processed by said processor (20A, 20B) determining a quality value (V) for said pavement distance (X) based on a relationship value (PDIn) which is related to the dispersion of the average temperature ranges (TIm) widthwise of said path (X).

21 Claims, 3 Drawing Sheets

(51) Int. Cl.
*G01N 25/72* (2006.01)
*G01N 33/42* (2006.01)

(56) References Cited

U.S. PATENT DOCUMENTS

2009/0142133 A1   4/2009   Caterpillar
2014/0308073 A1   10/2014  Voegele
2014/0308074 A1   10/2014  Rutz

FOREIGN PATENT DOCUMENTS

WO   00/70150   11/2000
WO   0070150    11/2000

OTHER PUBLICATIONS

Search Report issued in corresponding Russian Patent Application No. 2017144240/03, dated Sep. 12, 2019, pp. 1-3, and English translation pp. 1-2.
Office Action issued in corresponding Chinese Patent Application No. 201680033914.5, dated Jul. 3, 2019, pp. 1-6, and English translation pp. 1-9.
International Search Report issued in PCT/EP2016/062647 dated Jul. 21, 2016, pp. 1-2.
Written Opinion issued in PCT/EP2016/062647 dated Jul. 21, 2016, pp. 1-6.

* cited by examiner

METHOD OF DETERMINING THE QUALITY OF A NEWLY PRODUCED ASPHALT PAVEMENT

TECHNICAL FIELD

The present invention relates to a method of determining the quality of a newly laid asphalt pavement and preferably also for forecasting the life of a newly laid asphalt pavement.

In the present context, the term "asphalt" is intended to mean a mixture consisting of mineral aggregate bound together with asphalt.

BACKGROUND ART

Upon asphalting of a surface, homogeneousness is important, since it is the worst parts that initiate maintenance measures. In practice, it is impossible to improve the quality of an asphalt pavement at ambient temperature. Thermographic photographing reveals segregation problems, which may be caused by the asphalt plant, the transport of the asphalt out on the road, or practical measures in connection to the change from one lorry batch to the next one. Measured results can be used for improvements in the asphalt plant or to revised routines. Results from thermographic measurements can lead to a reward or reduced remuneration for the asphalt laying carried out.

U.S. Pat. No. 6,122,601 (Swanson et al.) discloses a compacted material density measurement and compaction tracking system, namely a two component system to obtain uniform density of compacted materials and track the compaction of the materials. The first component provides an automated, real-time compaction density meter and method of use to measure the density of the compacted material. The second component provides a Geographic Information System (GIS) for tracking compaction of a surface at specific locations. The two components of the present invention combined provide a system to measure the density of the compacted material and record the location of each density measurement. The components of the present invention can be utilized for many compaction operations, such as the roller compaction of concrete, pavement, soil, landfills, and asphalt pavements.

A CDS (Compaction Documentation System) was developed in the mid-'80s in Sweden (The Geodynamic Compaction Documentation System. Sweden: GEODYN, Inc., 1995). This CDS provides a conceptual system to monitor the compaction process. In this system, the operator enters the compaction data manually when he operates the compactor. All records, including lane change, direction change, number of passes, layer number, and start or stop to operate must be entered by hand. Moreover, there was no sensor to identify the orientation and position of moving compaction equipment, so operators must follow the moving path that was decided previously.

The technology of automated real-time positioning has improved tremendously in the last few years. Currently, there are two main modes for positioning, laser and GPS. Laser positioning is extremely accurate (<10 cm), however, it is limited by the need to place multiple laser targets that act as receivers. GPS is a satellite based technology. It is relatively inexpensive however accuracy is typically 3-5 meters, which is insufficient for this research. Through the use of differential GPS, the accuracy is improved to <1 m which is still unacceptable. However, with the application of software corrections, GPS differential measurements (GNSS) can have an accuracy of <10 cm.

Further, US 2014/0308074 (Rutz et al.) discloses a road finishing machine with a thermographic device releasably fixed to a portion of the machine for recording a georeferenced thermographic data record of at least one region of a pavement layer. The thermographic device includes a housing in which a detection unit for detecting a thermographic data record and a further detection unit for detecting a space-related data record for the thermographic data record are disposed.

In none of the known methods there is given any reliable quality measurement that preferably may easily be related to the actual lifetime of a newly laid asphalt pave.

SUMMARY OF THE INVENTION

It is an object according to the invention to provide a method that in reliable manner can be used for determining the quality of the newly produced asphalt pavement, as defined in claim 1.

Thanks to the invention it is achieved a method by means of which it is possible to process a large amount of scanned/recorded data in real time and to make adequate comparison of data parameters that are relevant regarding quality and which parameter may be further processes to establish a relationship value (PDI) that easily can be used to determine the quality, preferably also to make a forecast of the life time of the newly produced asphalt pavement.

Further advantages and preferred embodiments according to the invention will be described in the following detailed description of the invention, which shall not be construed to have any limiting effect in relation to the scope of claims. As is evident for the skilled person the basic principles according to the invention may be used in a variety of actual method steps.

BRIEF DESCRIPTION OF THE DRAWINGS

In the following, the invention will be described in more detail with reference to preferred embodiments and the appended drawings, wherein.

DETAILED DESCRIPTION OF THE INVENTION

Figure 1:
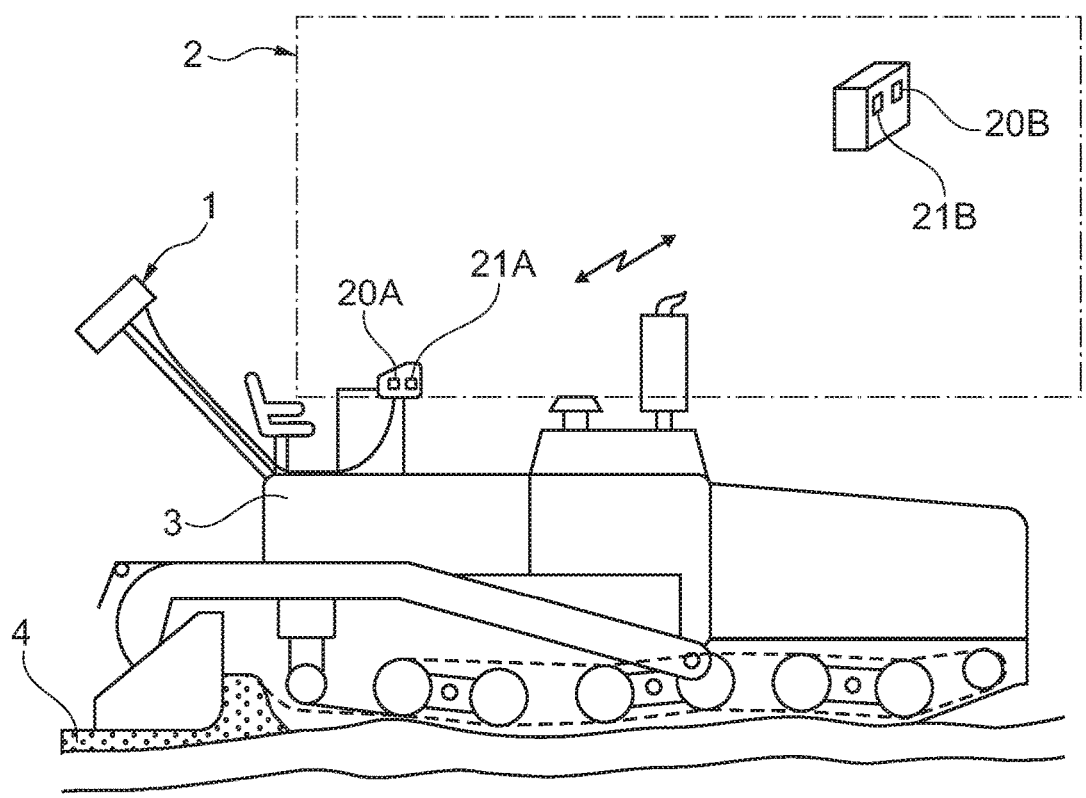
FIG. 1 is a schematic view of an arrangement in accordance with a schematically shown embodiment of the invention, showing a road finishing machine and a preferred set of a computer arrangement.

In FIG. 1 there is shown a road finishing machine 3 arranged with a sensor 1, for scanning the temperature of an asphalt pavement 4 directly after laying of the asphalt pavement. The sensor 1 preferably is in form of line scanner that measures the IR radiation. To cover the whole width W of the pavement that is produced a line scanner 1 need to be positioned on a sufficiently high level to be able to scan the whole width W. In the preferred embodiment the line scanner 1 has a registration window of 90°. Accordingly, it scans analogously the temperature across the whole width W of the pavement from one side of the registration window to the other side. In order to be able to scan also very broad pavements 4 the scanner 1 preferably has an attachment arrangement that allows for a positioning of 6 meters above the surface. In a preferred embodiment the sensor 1 is adjustably attached height wise to be able to adjust the vertical position of the sensor 1. The scanner has a sensor mechanism that rotates to scan within the scanning window (90°), which normally will rotate at a speed of about 10-200 revolutions per second. In a preferred embodiment, as will be used here in below, a frequency of 20-60 hertz is used, e.g. 40 revolutions per second.

The scanner 1 is connected to a first processor 20A and a first memory 21A. For each revolution that the scanner 1 performs the scanned temperature values Tn will be handled by the first processor 20A and stored in the memory 21A, in the preferred embodiment 512 values/revolution, normally within the range of 256-2048, are registered by a local processor (not shown) within the scanner 1. The first processor 20A is also connected to either distance measuring device (not shown, e.g. a wheel) that continuously measures the distance over time for the road finishing machine 3 and/or GPS equipment that continuously registers the position of the road finishing machine 3 and/or some of the kind either speed measuring device or distance measuring device. Accordingly, the first processor 20A is also given data regarding location of the road finishing machine 3 and thereby also the sensor 1 in a more or less continuous manner to store that data in relation to each registered analog temperature interval Ti. Accordingly, there is an exact storing, in the first memory 21A, of each scanned temperature interval Ti and its location, both length wise (by knowing the exact position of the machine) and crosswise (by having registered exact at what angle the different temperature values Tn are registered).

Figure 2:
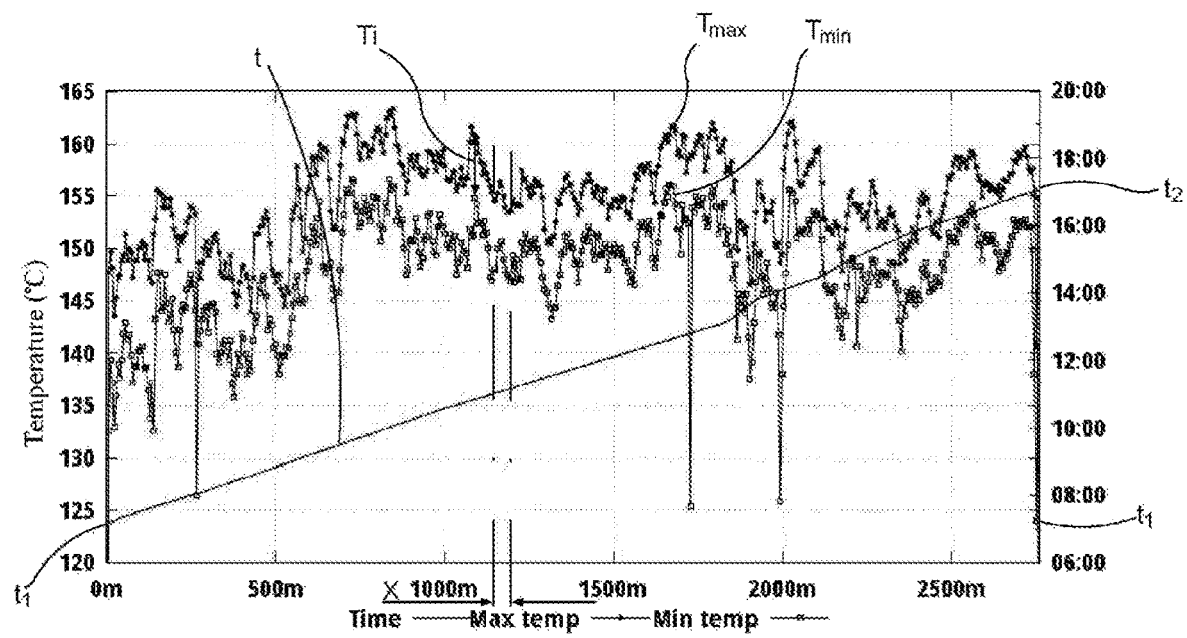
FIG. 2 shows a diagram presenting maximum registered temperature and minimum registered temperature and also the time for a newly produced pavement distance of about 2800 meter.

In FIG. 2 there is shown a diagram presenting different graphs. One graph Tmax that shows the maximum temperature measured by the sensor 1 and second temperature graph Tmin showing the minimum temperature registered by the sensor 1, wherein each value relates to a specific location of the whole distance that has been scanned. Further it is shown a graph presenting the time from start t1 of producing the pavement distance 1 until end t2 of producing the pavement distance. In FIG. 2 these data relate to a total distance of 2800 meter and it is shown that it took about 10 hours to produce those 2800 meter and further that the maximum temperature along the distance was about 163° and the minimum temperature about 125° respectively.

Figure 3:
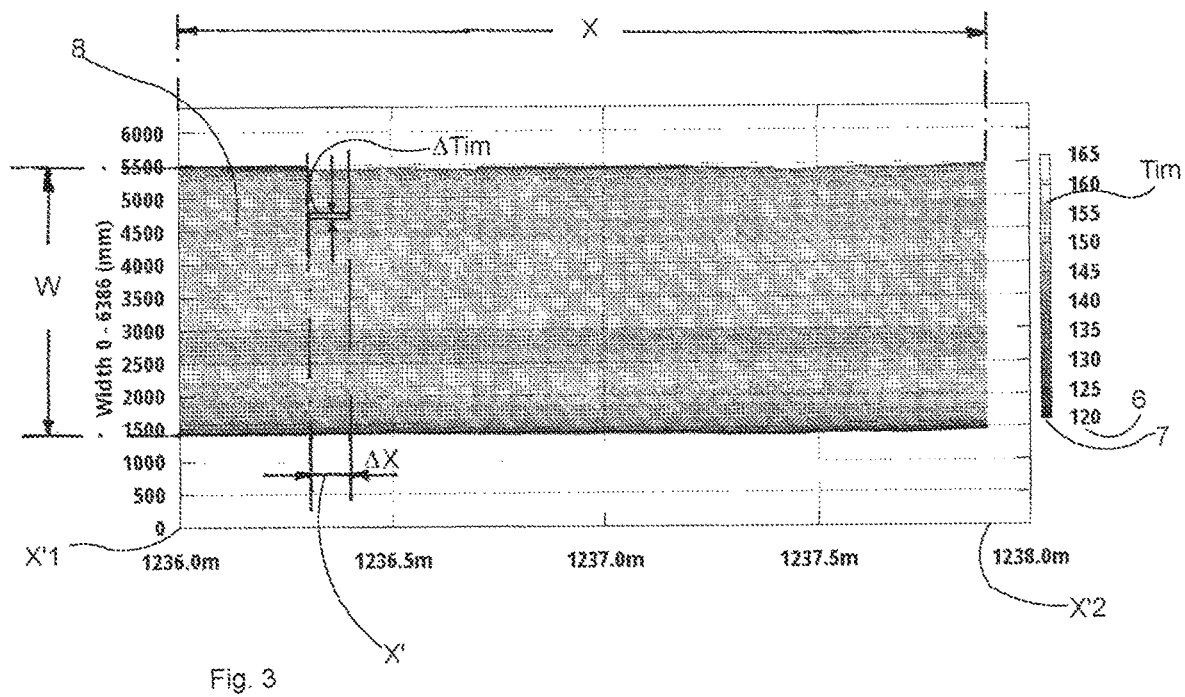
FIG. 3 is a zoomed in part of the diagram of FIG. 2, merely presenting a distance of 2 meters.
Figure 4:
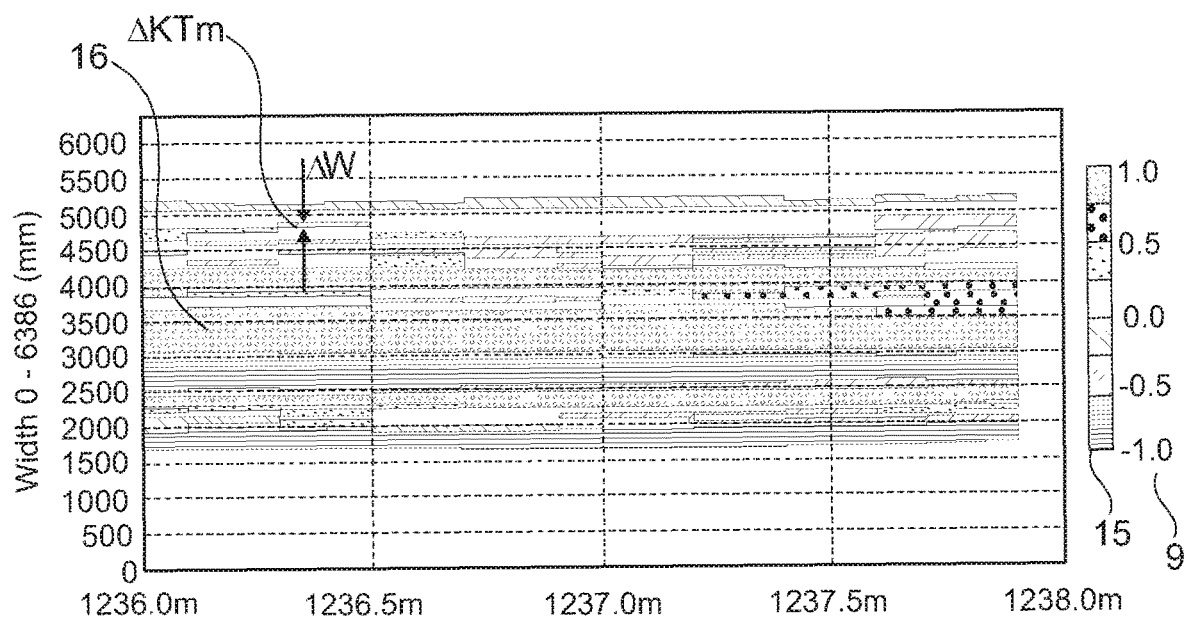
FIG. 4 is a diagram presenting all average temperature intervals distributed along the width of the same part of pavement as in FIG. 3.

In FIGS. 3 and 4 there is shown a partial distance X of the total distance presented in FIG. 2, ranging from 1236 meter to 1238 meter, where the maximum temperature Tmax was about 157° and that minimum temperature was about 150°. In the preferred embodiment each distance X is divided in to sections ΔX, and the average scanned temperature interval Tim for each section ΔX is used, for further processing, whereby all temperature intervals are stored in the first memory 21A and processed by the first processor 20A when a section ΔX is finished. In FIG. 4 it is shown picture 8 which indicates the average temperature intervals Tim for each section ΔX distributed along the width W of the pavement 4. The grey shade within the picture 8 is correlated to a certain temperature, as is shown in the temperature scale 6-7 presented in the right hand column next to the picture 8. When comparing with the grey shades within the picture 8 it can be seen that it very well corresponds to the above mentioned temperature range, i.e. a variation of temperatures crosswise in a range of about 150-157°.

Furthermore FIG. 1 shows that there is a connection between the first processor 20A and a second processor 20B, which second processor 20B is connected to a second memory 21B.

Figure 5:
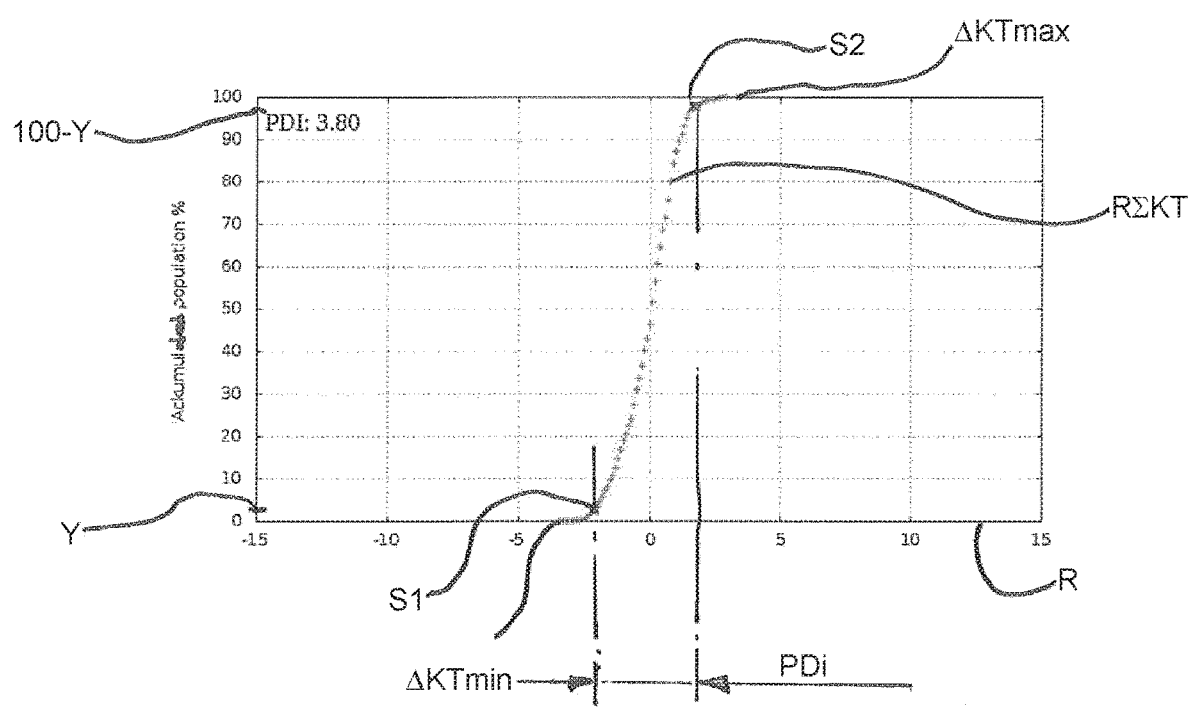
FIG. 5 is a presentation of the relationship value PDI for the part of the pavement referred to in FIGS. 3 to 4.

In FIG. 4 it is shown that the data (at least momentarily stored in the first memory 21A) as shown in FIG. 3, have been transferred to the second processor 20B and the second memory 21B connected there to for further processing. This further processing of the first data (as presented in FIG. 3) is based on determining for each given subsection ΔX the distribution of the different measured temperatures Tm in relation to its deviation from an average temperature Tm within that subsection ΔX, as is explained more in detail below. Accordingly a division of the measured temperature range Tim is performed wherein the whole range is divided in to absolute sub ranges ΔTim. These sub ranges ΔTim are in turn sorted in to classes ΔKTm, in relation to how far away from the average temperature Tm within that subsection ΔX the absolute sub range ΔTim is positioned. Finally all the sub ranges ΔTim are sorted in to a respective class ΔKTm. As shown in the picture 16 and the bar 15 in FIG. 4 each class ΔKTm have been given its own first line marking, wherein, as in FIG. 3 the intensity range is more or less presenting a continuous change. In FIG. 5 it is shown that there is a 0 level, representing the class ΔKTm that coincides with the average temperature Tm within each cross section ΔX. This class is chosen to be white. A class ΔKTm positioned farther away from the average temperature Tm within each sub section ΔX in a direction warmer than the average temperature Tm is indicated by a first line marking continuously darkening at the upper area of the bar 15, whereas in an opposite manner the same applies for classes representing a lower temperature than the average temperature then continuously shading into darker nuance of a second line marking. The picture 16 presented in FIG. 4 therefore shows for each sub section ΔX how the different classes ΔKTm are distributed along the width W.

In FIG. 5 there is shown a graph RΣKT wherein all the data presented in FIG. 4 have been compiled in to a diagram presenting a quality value for the pavement distance X of FIGS. 3 and 4. Accordingly the whole population of classified values ΔKTm have been summarized and by cutting out a chosen population value 2Y from said compilation an adequate value is presented that can be set in relation to the actual quality of the asphalt produced for the distance X. Hence, by taking away a chosen amount of the total population, e.g. 5% and merely using those values of the population in the remaining part of the population, that is positioned closer to the average of the population, a reliable value may be established, here called PDI. In the preferred embodiment this population share value Y is in the interval of 1-4%, but may of course be both smaller and larger if desired. In the shown example a value of about 4,6 is obtained for PDI, which is an indication of high quality of the pavement for the checked distance X. Empirical data and tests has shown that in average a PDI of about 10 is to be expected for a pavement living up to the forecasted lifetime, e.g. 10 years. A lower value indicates higher quality and a value above 10 indicates worse quality, V.

In the following it will be referred to example presenting the different steps in more detail.

When performing the method according to the invention, i.e. to determine the quality of a chosen part X of an asphalt pavement 4, the method may in the preferred embodiment comprise the following steps:

a) connecting the line scanner 1 to the processor arrangement 2, to be ready/stand by when the machine 3 starts moving, i.e. producing an asphalt pavement 4. In a preferred embodiment the processor arrangement 2 comprises a first local processor 20A and memory 21A arranged at the machine 3 and a second remote processor 20B and memory 20A, e.g. a remote server unit 20B/21B being continuously supplied with data from the local unit 20A/21A, e.g. position data X', time t, speed, etc. In FIG. 3 it is shown that the chosen part X is a fraction of the whole distance of that shown in FIG. 2, i.e. the chosen part X runs from X'1 1236 meters to X'2 almost 1238 meter. Hence a pavement distance X of about 2 meters.

b) continuously having the sensor 1 scanning and registering a number P of individual temperature ranges TIn for a number P of sub-section $\Delta X'$ within a predetermined section $\Delta X$. In tests that have been performed a line scanner 1 has been used as sensor 1 operating at 40 Hz and each sub-section $\Delta X'$ chosen to correspond to 2 seconds, (which normally corresponds to about 200 mm) implying that P will equal 80. Hence 80 subsequently scanned analog temperature ranges TIn will be stored in the memory 21A.

c) compiling said temperature ranges TIn for said section $\Delta X$ distributed along said width W, by means of retrieving them from the memory 21A and processing them in the processor 20A, d) determining and storing in the memory 21A an average temperature range TIm (see the grey shaded surface 8 in FIG. 3) presenting an average temperature range TIm for the said number P of compiled temperature ranges TIn, distributed along said width W of said section $\Delta X$. In the preferred embodiment, when the processor arrangement 2 comprises a second remote processor unit 20B/21B, this data is supplied to the second remote processor unit 20B/21B at this stage of the process, i.e. storing in the remote processor unit 20B/21B each compiled average temperature range TIm together with other desired supplied data, i.e. the location of the section $\Delta X$, etc. In FIG. 3 at the right hand side it is shown a temperature scale 6 running vertically from 120-165 C.° which is also transformed into a parallel positioned grey shade scale 7, running from darkest shade (120 C.°) to brightest shade (165 C.)°, via a central intermediate shade field (145 C.°) and shading into each other in the intermediate zones. Hence, the picture 8 presents that each sub-value $\Delta$TIm is given a specific grey shade corresponding to the above. In FIG. 3 this is exemplified by showing one sub-value $\Delta$TIm at a location X' within an example section $\Delta X$ and that the grey shade of that corresponds to a temperature TIm of about 157 C.°.

e) then steps b to d are repeated until all of said pavement distance X is produced, and the second, remote unit 20B/21B having all data as presented in FIG. 3 stored therein, f) determining and storing a temperature average value Tm for each of said average temperature ranges TIm, which preferably is achieved by processing and storing in the remote unit 20B/21B, g) dividing each average temperature range TIm into sub-values $\Delta$TIm classifying each sub-value $\Delta$TIm into a sub-classes $\Delta$KTn, wherein all sub-classes cover the whole range TIm of temperature for each section $\Delta X$, and storing the position X', $\Delta$W and sub-class $\Delta$KTn for each sub-values $\Delta$TIm, h) determining and storing a relative distance R, preferably as a percentage, to the average temperature Tm of each sub-value $\Delta$TIm for each section $\Delta X$. In FIG. 5, there is a scale 9 running vertically from −1 to +1, representing that relative distance R, which is also transformed into a parallel positioned scale 15, running from high intensity of the second line marking (e.g. representing −1 in FIG. 5) to high intensity of the first line marking (e.g. representing +1 in FIG. 5), via a central zero (0 which equals the average temperature Tm) that is white, and shading into each other in the intermediate zones. This is exemplified in FIG. 5, by showing the same sub-value $\Delta$KTm as in FIG. 4 and that the marking of that (low intensity second line marking) corresponds to a relative distance R of about −0,2°. When presenting all that stored data as a picture 16, as in FIG. 5, it is shown for each sub-value $\Delta$TIm how much, and in what direction (colder=second line marking, hotter=first line marking) it deviates from the average temperature Tm and also its location. Since the quality is very much related to the dispersion of temperature along the width W, this picture 16 gives very useful information to the skilled person regarding the quality of the shown asphalt pavement distance X. As is evident for the skilled person a short distance X (as the 2 meters in FIG. 5) will most likely present a relatively small range of relative distance R, i.e. about 2 as shown in FIG. 5, whereas a bigger range (e.g. of about 5 to 15) most likely will be obtained if a larger distance is investigated.

Now the quality may be determined further by determining a quality value V for said pavement distance X that is easy to understand for anybody. Such a quality value (V) is according to the preferred mode of the invention based on a relationship value PDIn which is related to the dispersion of the sub-values $\Delta$TIm widthwise of said pavement distance X, preferably including the further steps;

i) sorting the population of all sub-values $\Delta$TIm based on sub-class $\Delta$KTn for the pavement distance X in relation to the relative distance R of each sub-value $\Delta$TIm and determining the relative proportions R$\Sigma$KT, preferably a percentage, of the number of sub-values $\Delta$TIm at each relative distance R for said pavement distance X, k) summing up the accumulated relative proportions R$\Sigma$KT within said pavement distance X, from the lowest class $\Delta$KTmin to the highest class $\Delta$KTmax. As shown in FIG. 5 this may be plotted into a graph, where the accumulated figures R$\Sigma$KT are presented on the Y-axis (0-100) and the relative distance R on the X-axis (−15 to +15), l) determining a population share value Y, m) using said population share value Y to determine a first partial value YKT constituting a lower partial value S1 and for determining a second partial value KT-YKT constituting an upper partial value S2 of the summed accumulated relative shares R$\Sigma$KT n) determining the distance PDI between said lower partial value S1 and said upper partial value S2. In FIG. 5 it is shown that a PDI of about 3,2 is obtained.

Now that distance PDI may be easily compared with an empirically predetermined correlation distance PDIj, on the understanding that if PDI=PDIj an acceptable quality value Va is indicated and if PDI<PDIj indicated a better quality value V than said acceptable quality value Va is indicated. Test have shown that the use of PDIj of about 10 in most cases may be used. Accordingly, a PDI of about 3, 2 indicates a very high quality.

To make the method even more sophisticated it is feasible to further calculate a relative quality value Vr, wherein Vr=k PDIj −PDIn/PDIj where k indicates a selected multiplier, and a positive relative quality value Vr demonstrating a relative quality value V that is better than the acceptable quality value Va and with increasing quality value Vr, the higher the value is, respectively a negative relative quality value Vr indicating a relative quality value that is not acceptable and of a lower quality, the higher the negative is.

Moreover, a supposed lifetime value Q of said asphalt pavement may be determined for said path X by relating said relative quality value Vr to an average lifetime value Qa.

The invention is not limited to what is defined above but may be varied within the scope of the claims. For instance, it is evident that the sensor 1 may be positioned on a separate vehicle, i.e. not the road finishing machine, e.g. a roller following the road finishing machine. Further it is evident that many of the expression used are in no way limiting, e.g. that the relationship value may take other formats than the one exemplified above.

The invention claimed is:

1. A method to determine the quality of an asphalt pavement, the method comprising the steps of:
    a) providing and initializing at least one sensor connected to a processor arrangement comprising at least one processor connected to at least one memory, for recording at least the temperature values (Tn), time (t) and/or position (X) momentarily for the entire width (W) of an asphalt pavement in connection with its production along a pavement path (X);
    b) scanning and registering a number (P) individual temperature ranges (Tin) for a number (P) of the section ranges ($\Delta X'$) in a section ($\Delta X$);
    c) compiling said temperature ranges (Tin) in said section ($\Delta X$) distributed along said width (W);
    d) determining and storing in said memory an average temperature range (Tim) presenting an average temperature range (Tim) for the said number (P) of compiled temperature ranges (Tin) distributed along said width (W) of said section ($\Delta X$); and
    e) repeating steps b) to d) until all of said pavement distance (X) is produced, wherein said stored average temperature ranges (Tim), in said memory, are processed by said processor determining a quality value (V) for said pavement distance (X) based on a relationship value (PDIn) which is related to the dispersion of the average temperature ranges (Tim) widthwise of said path (X), wherein said quality determining comprises the following steps;
    f) determining and storing a temperature average value (Tm) for each of said average temperature ranges (Tim), and
    g) determining and storing the relative distance (R) to the average temperature (Tm) of sub-values ($\Delta$TIin) obtained by dividing each average temperature range (Tin) within each section ($\Delta X$) into said sub-values ($\Delta$TIin).

2. The method of claim 1, further comprising calculating a relative quality value (Vr), wherein Vr=k (PDIj–PDI)/PDIj where k indicates a selected multiplier, and a positive relative quality value (Vr) demonstrating a relative quality value (V) that is better than the acceptable quality value (Va) and with increasing quality value (Vr), the higher the value is, respectively a negative relative quality value (Vr) indicating a relative quality value that is not acceptable and of a lower quality, the higher the negative is.

3. The method according to claim 1, wherein said section ($\Delta X'$) is in the range 50-600 mm.

4. The method according to claim 1, wherein the number (P) scanned and registered individual intervals ($\Delta$In) within said section ($\Delta X$) is between 50 and 500.

5. The method according to claim 1, wherein said population share value (Y) is in the range 0.01 to 0.04.

6. The method according to claim 1, wherein each said class ($\Delta$KTn) constituting an absolute range value ($\Delta$TI) in the range of 0.0005-0.002 of the registered average temperature range (Tim) of said section (X).

7. The method according to claim 1, wherein said sensor is an infrared line scanner arranged to scan said temperature range ($\Delta$In).

8. The method according to claim 7, wherein said sensor comprises a rotating member which scans the IR values within a certain angle range (a), which is 60<a<120.

9. The method according to claim 7, wherein said sensor is arranged 2-6 m above the surface of said asphalt pavement.

10. The method according to claim 7, wherein said sensor comprises a rotating member which scans the IR values within a certain angle range (a), which is 80<a<100°.

11. The method according to claim 1, wherein said sensor is an infrared camera arranged to scan said temperature range (Tin).

12. The method according to claim 1, wherein said processor arrangement comprises at least a first processor and a first memory adapted to process said average temperature ranges (Tim) and a second processor and a second memory arranged to determine the relative value (PDIn).

13. The method according to claim 12, wherein said second processor and second memory constitute a server unit, preferably placed at a remote place in relation to said sensor.

14. The method according to claim 1, wherein the position for each measurement is determined by a GPS receiver.

15. The method according to claim 1, further comprising directly after compaction of the asphalt pavement, continually measuring a density of the compacted asphalt pavement and recording the density data.

16. The method according to claim 15, wherein the density is estimated from a measurement of a surface temperature of the compacted asphalt pavement.

17. The method according to claim 1, wherein said section ($\Delta X'$) is in the range 100-300 mm.

18. The method according to claim 1, wherein the number (P) scanned and registered individual intervals ($\Delta$In) within said section ($\Delta X$) is 60 to 200.

19. The method according to claim 1, wherein the number (P) scanned and registered individual intervals ($\Delta$In) within said section ($\Delta X$) is 70 to 100.

20. The method according to claim 1, wherein said population share value (Y) is in the range 0.02 to 0.03.

21. A method to determine the quality of an asphalt pavement, the method comprising the steps of:
    a) providing and initializing at least one sensor connected to a processor arrangement comprising at least one processor connected to at least one memory, for recording at least the temperature values (Tn), time (t) and/or position (X) momentarily for the entire width (W) of an asphalt pavement in connection with its production along a pavement path (X);
    b) scanning and registering a number (P) individual temperature ranges (Tin) for a number (P) of the section ranges ($\Delta X'$) in a section ($\Delta X$);
    c) compiling said temperature ranges (Tin) in said section ($\Delta X$) distributed along said width (W);
    d) determining and storing in said memory an average temperature range (Tim) presenting an average temperature range (Tim) for the said number (P) of compiled temperature ranges (Tin) distributed along said width (W) of said section ($\Delta X$); and
    e) repeating steps b) to d) until all of said pavement distance (X) is produced, wherein said stored average temperature ranges (Tim), in said memory, are processed by said processor determining a quality value (V) for said pavement distance (X) based on a relationship value (PDIn) which is related to the dispersion of the average temperature ranges (Tim) widthwise of said path (X), wherein said quality determining comprises the following steps;

f) determining and storing a temperature average value (Tm) for each of said average temperature ranges (Tim), and g) determining and storing the relative distance (R) to the average temperature (Tm) of sub-values (ΔTIiη) obtained by dividing each average temperature range (Tin) within each section (ΔX) into said sub-values (ΔTIiη), h) sorting the population of all sub-values (ATIm) into classes (ΔKTη) for the pavement distance (X) and determining the relative proportions (RΣKT), preferably a percentage, of the number of sub values (ATIm) at each relative distance (R) for said pavement distance (X), i) summing up the accumulated relative proportions (RΣKT) within said pavement distance (X), from the lowest class (AKTmin) to the highest class (AKTmax), j) determining a population share value (Y), k) using said population share value (Y) to determine a first partial value (YKT) constituting a lower partial value (S1) and for determining a second partial value (KT YKT) constituting an upper partial value (S2) of the summed accumulated relative shares (RΣKT), n) determining the distance (PDI) between said lower partial value (S1) and said upper partial value (S2), and o) comparing the distances (PDI) with an empirically predetermined correlation distance (PDIj), on the understanding that if (PDI)=(PDIj) an acceptable quality value (Va) is indicated and if (PDI)<(PDIj) indicated a better quality value (V) than said acceptable quality value (Va) is indicated.

* * * * *